US00PP25766P3

(12) United States Plant Patent
Cain

(10) Patent No.: US PP25,766 P3
(45) Date of Patent: Aug. 4, 2015

(54) GRAPEVINE 'IFG FIFTEEN'

(50) Latin Name: *Vitis vinifera*
Varietal Denomination: IFG Fifteen

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 216 days.

(21) Appl. No.: 13/986,678

(22) Filed: May 24, 2013

(65) Prior Publication Data

US 2014/0352008 P1 Nov. 27, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Fifteen'. The new grapevine is characterized by producing medium size, oval, completely black berries having medium firm texture with a mild muscat flavor and which ripens in early midseason.

2 Drawing Sheets

Latin name of the genus and species claimed: *Vitis vinifera.* Variety denomination: 'IFG Fifteen'.

BACKGROUND OF THE INVENTION

The new and distinct grapevine described and claimed herein originated from a hand pollination of the Princess variety (USDA non-patented) and the Fantasy variety (USDA non-patented) hybridized in May 2003. The abortive seed traces were subsequently embryo cultured and the resulting plant was planted in the field in April 2004. The present variety of grapevine was selected as a single plant in July 2005 and was first asexually propagated by hardwood cuttings in December 2005 near Delano, Kern County, Calif. The resulting propagules were planted during April 2006 at the International Fruit Genetics LLC research facility near Delano, Kern County, Calif. and were found to reproduce true-to-type through at least one generation of asexual reproduction.

BRIEF SUMMARY OF THE INVENTION

The new grapevine 'IFG Fifteen' is characterized by producing medium size oval completely black berries having medium firm texture with a mild muscat flavor and which ripens in early midseason. Berries are borne on medium size clusters which are moderately compact and require gibberellin applications to thin clusters and size berries. Berries color extremely well and do not require chemical applications to achieve full black color. To the inventor's knowledge, the known variety to which the new grapevine variety is most similar is the Summer Royal variety (non-patented). 'IFG Fifteen' differs from the Summer Royal variety by ripening approximately one to two weeks later, and having a mild muscat flavor as opposed to the neutral flavor of 'Summer Royal'. Berries of 'IFG Fifteen' are smaller than 'Summer Royal' and the stem is stronger and more lignified.

'IFG Fifteen' differs from its maternal parent, the Princess variety (USDA non-patented) by producing full black, small obtuse ovate berries as opposed to the large white more blocky cylindrical berries of the Princess variety. It differs from its pollen parent, the Fantasy variety (USDA non-patented) by having earlier ripening, small black berries with a mild muscat flavor as opposed to the later ripening, large black neutral flavored berries of 'Fantasy'.

BRIEF DESCRIPTION OF THE FIGURES

The accompanying photographic illustrations in FIG. 1 and FIG. 2 illustrate in full color 'IFG Fifteen'.

DETAILED BOTANICAL DESCRIPTION OF THE INVENTION

Figure 1:
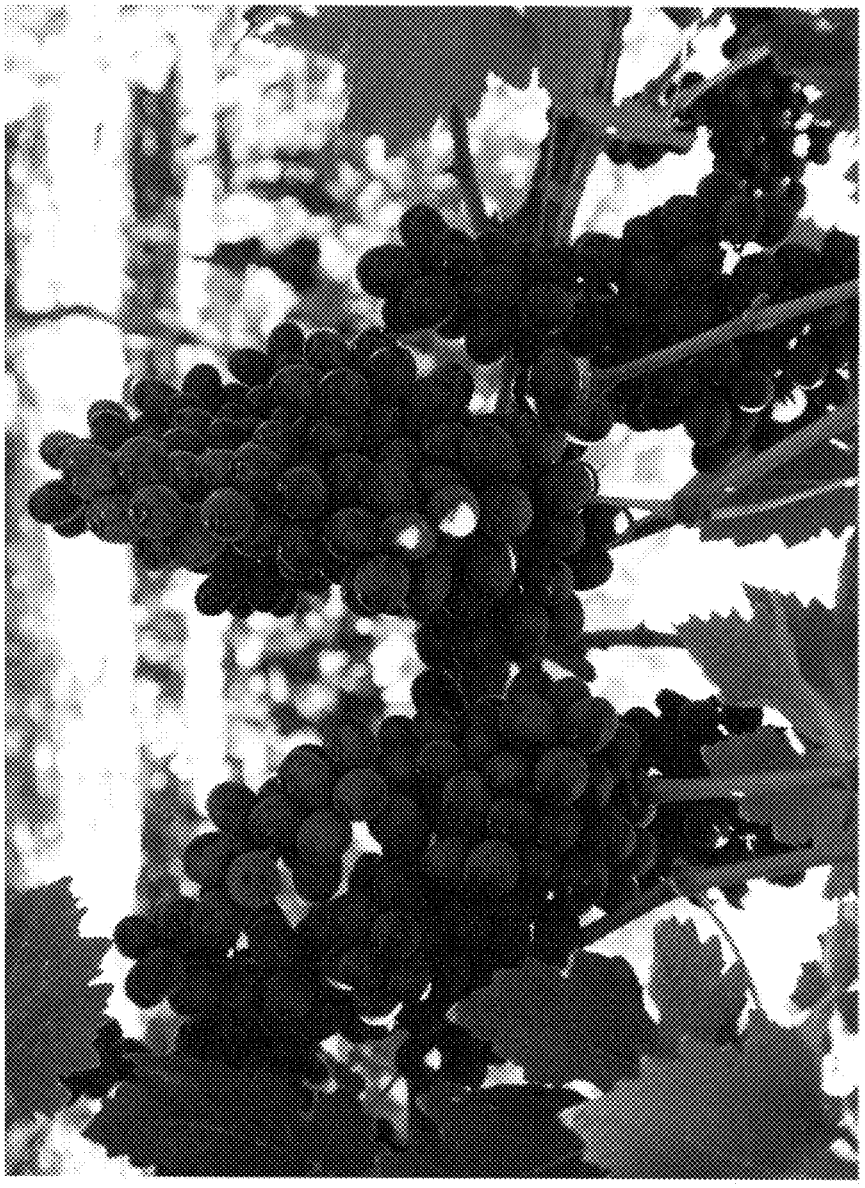
FIG. 1 shows fruit clusters on the vine.
Figure 2:
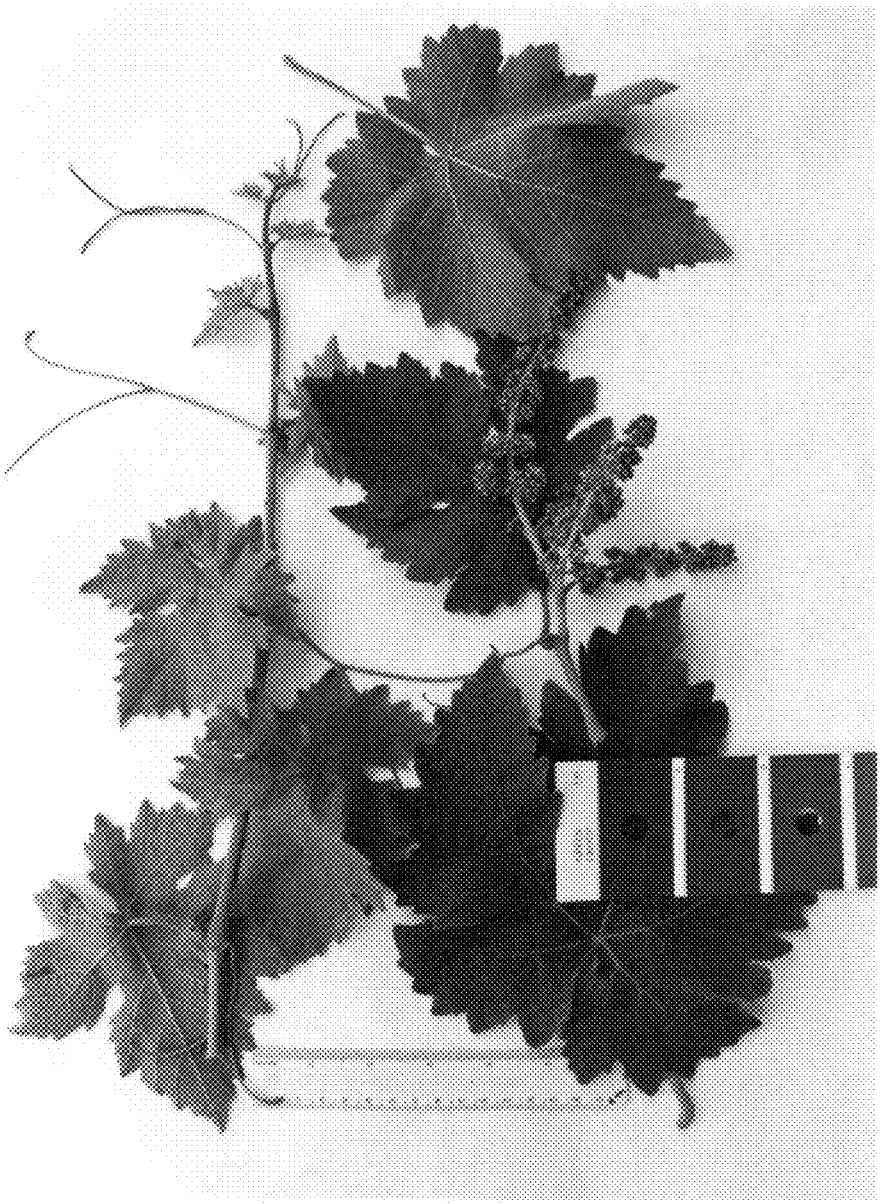
FIG. 2 shows mature leaves, a young shoot tip and flower. The photographs were taken outdoors with indirect lighting. The colors are as nearly true as is reasonably possible in a color representation of this type.

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Fifteen' plants grown in the vicinity of Delano, Kern County, Calif. during 2009 to 2011, and is believed to apply to plants of the variety grown under similar conditions of soil and climate elsewhere:

Vine:

*General*.—Size — Large. Vigor — Medium. Density of foliage — Medium dense. Productivity — Medium productive. Root stock — Own root. Training method — Typically spur pruned leaving 2 bud spurs.

*Trunk*.—Trunk diameter of 4-year-old vines at 30 cm above the soil line — 5.4 cm. Shape — Medium. Straps — Short — Split. Surface texture — Shaggy. Inner bark color — Can be any of the following colors; Greyed orange; 177A and B and D.

Shoots:

*Young shoot*.—Form of tip — Fully opened. Distribution of anthocyanin coloration of tip — Piping (striped). Intensity of anthocyanin coloration of tip — Very weak. Density of prostrate hairs of tip — Medium dense. Density of erect hairs of tip — Absent. Color — Can be any of the following colors; Yellow green; 146C and 144A.

*Woody shoot* (*mature canes*).—Shape — Medium thick. Internode length — Medium; About 13.0 cm. Width at node — About 1.3 cm. Cross section — Elliptic. Surface — Edged. Main color — Can be any of the following colors; Grey orange; 175A and B and C. Density of erect hairs of nodes — None. Density of erect hairs on internodes — None. Growth of axillary shoots — Weak; Approximately 4.6 cm.

*Flowering shoot*.—Vigor during flowering — Medium to Strong. Attitude during flowering on shoots not tied — Semi-drooping to Drooping. Color — dorsal side of internodes — Green with Red stripes. Color — ventral side of internodes — Green with Red stripes. Color — dorsal side of nodes — Green with Red stripes. Color — ventral side of nodes — Green. Density of prostrate hairs of nodes — Very sparse. Density of erect hairs on nodes — None. Density of prostrate hairs on internode — None. Density of erect hairs on internode — None. Anthocyanin coloration of buds — Absent.

*Tendrils*.—Distribution on the shoot (at full flowering) — Discontinuous. Length of Tendril — Medium; About 18.4 cm. Thickness — Medium. Color — Can be any of the following colors; Yellow green; 144A and B. Form — Bifurcated. Number of consecutive tendrils — 2.

Leaves:

*Young leaves*.—Color of upper surface of first four distal unfolded leaves — Green. Average intensity of anthocyanin coloration of six distal leaves prior to flowering — Absent. Density of prostrate hairs between veins (lower surface) — Sparse. Density of prostrate hairs on veins (lower surface) — Sparse. Density of erect hairs between veins (lower surface) — Absent. Density of erect hairs on veins (lower surface) — Very sparse.

*Mature leaves*.—Average length — About 15.6 cm. Average width — About 18.7 cm. Mature leaf size — Large. Shape of blade — Pentagonal. Number of lobes — 5. Anthocyanin coloration of main veins on upper side of blade — Absent. Mature leaf profile — Undulate. Blistering surface of blade upper surface — Very weak. Leaf blade tip — In the plane of the leaf. Undulation of margin — Slight. Thickness — Medium. Undulation of blade between main and lateral veins — Absent. Shape of teeth — Mixture of both sides straight and both sides convex. Length of teeth — Medium. Ratio length/width of teeth — Medium. Shape of upper lateral sinuses — Lobes slight to strongly overlapping. Depth of upper lateral sinuses — Deep. General shape petiole sinus — Slightly open to Closed. Shape of base of upper leaf sinuses — U-shaped. Tooth at petiole sinus — Absent. Density of prostrate hairs between veins on lower surface of blade — Very sparse. Density of erect hairs between veins on lower surface of blade — Very sparse. Density of prostrate hairs on main veins on lower surface of blade — Very sparse. Density of erect hairs on main veins on lower surface of blade — Sparse to Medium. Density of prostrate hairs on main veins on upper surface of blade — Sparse. Density of erect hairs on main veins on upper surface of blade — None. Autumn coloration of leaves — Leaves can be a single color or combination of colors, in a mottled pattern or on the edges of the leaves; Greyed yellow; 163A and B and C, and 162A, and Greyed purple; N186C and 187A and B and C, and Greyed red; 181A and 183A and B and C.

*Upper surface*.—Color — Can be any of the following colors; Green; 137A and 139A. Anthocyanin coloration of main veins — Absent. Surface appearance — Dull. Blistering surface of blade — Very weak.

*Lower surface*.—Color — Can be any of the following colors; Green; 138A and 137C. Anthocyanin coloration of main veins (lower surface) — Medium. Glossiness — Weak. Surface texture — Smooth. Surface appearance — Dull.

*Petiole*.—Length — About 11.5 cm. Length of petiole compared to middle vein — Much shorter. Density of prostrate hairs on petiole — None. Density of erect hairs on petiole — None.

*Buds*.—Bud fruitfulness — Basal: Mostly fruitful. Position of first fruitful shoot on previous season cane — $2^{nd}$ to $3^{rd}$ node. Time of bud burst — Late; Mar. 10, 2011.

Flowers:

*General*.—Flower sex — Hermaphrodite. Length of first inflorescence — Medium; About 16.1 cm long by 10.2 cm wide. Position of first flowering and fruiting node — $4^{th}$ or $5^{th}$ node (current season growth). Number of inflorescence per flowering shoot — 1.1 to 2. Time of bloom — Midseason as compared with similar varieties in the growing area of Delano, Calif. Date of full bloom — May 17, 2011.

Fruit:

*General*.—Ripening period — Early; Approximately Aug. 8, 2011. Use — Fresh market. Keeping quality — Excellent. Resistance to — Insects: Average typical of *Vitis vinifera* species. Diseases: Average typical of *Vitis vinifera* species. Refractometer test — Soluble solids: About 21.4 Brix. Brix/acid — About 38.9. Titratable acidity — About 0.55 g/100 ml. Juice pH — About 3.63.

*Cluster*.—Mature cluster length (peduncle excluded) — About 23.1 cm. Mature cluster width — About 13.7 cm. Mature cluster weight — About 560 g. Bunch density — Medium. Number of berries — About 149. Form — Conical.

*Peduncle*.—Lignification of peduncle — Weak. Length of peduncle — Medium. Approximately 2.5 cm.

*Berry*.—Uniformity of size — Uniform. Single berry weight — About 4.4 g natural; to about 5.2 g when treated with gibberellic acid. Shape — Obtuse ovate. Seeds — Contains small rudimentary seed traces. Cross section — Circular. Berry dimensions — longitudinal axis: About 2.1 cm. horizontal axis: About 1.9 cm. Berry firmness — Medium firm. Particular flavor — Mild Muscat. Bloom (cuticular wax) — Medium. Berry separation from pedicel — Medium. Skin color (without bloom) — Can be any of the following colors; Greyed purple; N186A and B.

*Skin*.—Thickness — Medium. Texture — Medium. Reticulation — Absent. Tenacity — Tenacious to flesh.

What is claimed:

1. A new and distinct variety of grapevine as herein illustrated and described.

* * * * *